United States Patent
Wilczok et al.

(10) Patent No.: US 6,403,851 B1
(45) Date of Patent: Jun. 11, 2002

(54) PROCESS FOR PREPARING CYCLODODECATRIENES WITH RECYCLING OF THE CATALYST

(75) Inventors: Norbert Wilczok, Muelheim; Thomas Schiffer, Haltern; Peter Wiedenbusch, Marl, all of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/615,911

(22) Filed: Jul. 13, 2000

(30) Foreign Application Priority Data

Jul. 13, 1999 (DE) .......................... 199 32 577
Jan. 21, 2000 (DE) .......................... 100 02 460

(51) Int. Cl.$^7$ .............................................. C07C 13/02
(52) U.S. Cl. ..................................... 585/366; 585/369
(58) Field of Search ................................. 585/366, 369

(56) References Cited

U.S. PATENT DOCUMENTS

| | | | |
|---|---|---|---|
| 3,235,613 A | * 2/1966 | Lapporte | .................... 260/666 |
| 3,644,548 A | 2/1972 | Takahasi et al. | |
| 3,655,795 A | 4/1972 | Sullivan et al. | |
| 3,723,553 A | 3/1973 | Wu et al. | ................ 260/666 B |
| 3,878,258 A | 4/1975 | Rapoport et al. | |
| 4,270,016 A | 5/1981 | Tolstikov et al. | ........... 585/360 |
| 5,932,687 A | 8/1999 | Baumann et al. | ........... 528/313 |

FOREIGN PATENT DOCUMENTS

| | | |
|---|---|---|
| DE | 12 83 836 | 11/1968 |
| DE | 19 42 729 | 2/1970 |
| DE | 19 46 062 | 4/1970 |
| DE | 28 25 341 | 12/1979 |
| DE | 30 21 795 | 12/1981 |
| DE | 30 21 840 | 1/1982 |
| JP | 05124982 A | * 5/1993 |
| NL | 6609061 | 6/1966 |

OTHER PUBLICATIONS

Ulf Schuchardt et al, "Highly Selective Cyclotrimerisation of Butadiene to Cyclododecatriene Catalyzed by Polymer-anchored Nickel (0)", *Journal of Molecular Catalysis*, 29, 1985, pp. 145–149.
*Angew. Chem.*, 69, 1957, Nr. 11, pp. 397–398.
Von H. Breil et al, "I. Mitt. Über die katalytische Unwandlung von Olefinen", *Synthese von Cyclododecatrienen—(1, 5,9)*, 1963.
Chemical Abstracts 119:72275s, Deactivation of catalysts in preparation of cyclododecatriene–1,5,9, Nobuaki Sanada et al.
*Angew Chem.*, 71, 1959, Nr. 18, p. 574. No English.
Yasushi Shiomi et al, "Catalyst deactivation in the manufacturre of 1,5,9–cyclododecatriene", JP 06–254398/CAN 121:303571.
Hiroshi Takahashi et al, "Catalyst for cyclic polymerization of butadiene", JP 7625439/CAN 86:17321.
Hiroshi Takashi et al, "Catalyst for cyclic polymerization of butadiene", JP 7625396/CAN 86:17322.
Isao Ono et al, "Cyclododecatriene", JP 7442496/CAN 82:139521.
Etsuro Kunioka et al, "Cyclododecatriene", JP 43013451/CAN 70:77450.

* cited by examiner

*Primary Examiner*—Thuan D. Dang
(74) *Attorney, Agent, or Firm*—Oblon, Spivak, McClelland, Maier & Neustadt, P.C.

(57) ABSTRACT

Cyclododecatrienes may be prepared in a continuous process by reacting 1,3-butadiene in the presence of a catalyst system and cyclooctadiene and/or cyclododecatriene. The resulting crude cyclododecatriene product may be separated from this mixture by distillation, and 50 to 100% of the catalyst system may be recycled back into the process.

19 Claims, 1 Drawing Sheet

US 6,403,851 B1

PROCESS FOR PREPARING CYCLODODECATRIENES WITH RECYCLING OF THE CATALYST

BACKGROUND OF THE INVENTION

1. Field of the Invention

The present invention relates to a preferably continuous process for preparing cyclododecatrienes (CDTs) over a catalyst system comprising, in particular, nickel or titanium, with removal of the crude cyclododecatrienes by distillation and recycling of the catalyst.

2. Description of the Background

The synthesis of CDT starting from 1,3-butadiene has been examined using both homogeneous and heterogeneous transition metal catalysts. In the case of heterogeneous catalyst systems, a transition metal complex is typically bound to a polymeric support via a bridging ligand (U. Schuchardt, J. Mol. Catal; 29 (1985) 145). Such fixed-bed systems have the serious disadvantage that the bridging ligand competes with butadiene, CDT and olefinic intermediates for a free coordination position on the catalyst. This competition considerably reduces the conversion rate of the fixed-bed catalyst, and the proportion of dimeric and/or oligomeric by-products generally increases. In addition, CDT can displace the bridging ligand from the transition metal. This displacement results in the metal atom being leeched from the fixed bed. The fixed-bed catalyst loses its active centers and its catalytic activity decreases.

Because of these problems, homogeneous catalysts rather than fixed-bed catalysts have generally become established in industrial-scale implementation of the synthesis. The advantages of homogeneous catalysts are, in particular, very good space-time yields and high selectivities in favor of CDT. Among the transition metals known in the literature (G. Wilke, Angew. Chemie 69 (1957) 397; H. Breil, P. Heimbach, M. Kröner, H. Müller, G. Wilke, Makromolekulare Chemie 69 (1963) 18; G. Wilke, M. Kroner, Angew. Chemie 71 (1959) 574), titanium, chromium and nickel compounds are used most often. These transition metals are catalytically active in the form of organometallic complexes in which the central atom is in the oxidation state 0. These organometallic complexes are typically prepared from a transition metal salt and a reducing agent. The reducing agent used is generally an organometallic compound of the first through third group of the Periodic Table. For the titanium catalysts widely used in industry, a useful route has been found to be, in particular, the reaction of titanium tetrachloride or titanium acetylacetonate with an organoaluminum compound (U.S. Pat. No. 3,878,258; U.S. Pat. No. 3,655,795, both of E.I. du Pont de Nemours; DE 30 21 840 and DE 30 21 791, both of Chemische Werke Huels), although numerous other titanium salts and reducing agents have also been described as starting compounds, e.g. DE 19 46 062, Mitsubishi Petrochemical Co. and U.S. Pat. No. 3,644,548, Asahi Chemical Industry.

In the industrial synthesis of CDT using a homogeneous catalyst, the reaction is usually conducted in a continuous process using one or more stirred vessels. Part of the reaction mixture is discharged continuously from the reactors. In the work-up, unreacted starting material is recovered and returned together with fresh butadiene to the reaction process. Part of the catalyst is also discharged together with the reactor output. The concentration of catalyst in the reactor is, therefore, usually kept constant by continuous addition of fresh catalyst constituents.

Before work-up of the reactor output, the catalyst which has been discharged has to be decomposed. Various polar solvents are very suitable for this purpose. Apart from water, Ube Industries use, for example, an ammonium hydroxide solution (JP 05-070377, JP 06-254398, both of Ube Industries, cited according to CA 119:72275 and CA 121:303571). Various alcohols (JP 07-625439, JP 07-625396, both of the Agency of Industrial Sciences and Technology, Japan, cited according to CA 86:17321 and CA 86:17322) are also suitable for this purpose. In particular, use is made of methanol (JP 07-442496, Toyo Soda Co., cited according to CA 82:139521) and methanolic hydrochloric acid (DE 19 42 729, Mitsubishi Petrochemical Co.).

The decomposition of the catalyst can also be conducted by means of acetone (JP 04-301345 1, Toyo Rayon, cited according to CA 70:77450) or by using a suspension of calcium oxide in water (NL 6 603 264, Shell Int. Research Maetschappij N.V.). Ube Industries comment that the CDT formed can be recovered only incompletely if water is used for decomposing the catalyst. However, the CDT yield can be improved if aqueous tetrahydrofuran is used (JP 05-070377, cited according to CA 119:72275).

All the above-mentioned examples of the homogeneously catalyzed CDT synthesis accept decomposition of the catalyst system during the work-up. Because of the high conversion rate and selectivity of the catalyst, the amounts of catalyst required compared to the amount of CDT formed are small, but an alternative work-up with recycling of the active catalyst would be desirable. This is particularly true of the two transition metals chromium and nickel because of the heavy metal contamination of the wastewater resulting from the work-up.

The industrial cyclodimerization of 1,3-butadiene to cyclooctadiene (COD) is conducted in the liquid phase over a nickel(0) complex. The homogeneous catalyst in this reaction comprises the transition metal and a bulky donor ligand, typically a phosphine or a phosphite. It is known that this catalyst system can be partly recovered and, therefore, used a number of times. For this purpose, the material discharged from the reactor is usually worked-up by fractional distillation. In this distillation step unreacted starting material, COD and low-boiling byproducts are separated. A relatively high-boiling residue remains in which the catalyst is present in dissolved form. This residue is returned to the reaction and the catalyst is used again for butadiene dimerization. Only after a number of cycles does the proportion of high boilers in the reaction mixture increase to such an extent that the catalyst has to be discharged with the high-boiling fraction and then must be discarded.

In the case of CDT (1,5,9-cyclododecatriene), which is formed as trans-trans-trans, cis-trans-trans and cis-cis-trans isomers, recycling of the catalyst on the industrial scale has not yet been described. Only a few examples, which were conducted batchwise and in which multiple use of the catalyst was attempted on a laboratory scale, are known. Thus, DE 30 21 791 A1 describes a process in which the catalyst is first adsorbed on activated carbon and is later removed by filtration together with the activated carbon. However, this process has not been found to be useful in industry, since the catalyst can be only partly recovered in this manner.

Example 3 of DE 12 83 836 describes a procedure in which the Ni(0)-COD complex after the reaction in the presence of the solvent benzene accumulates in the high-boiling bottom products of the distillation and still has a residual butadiene activity, so that it can be used once more upon recycling. However, no further information about catalyst recycling is given.

Example 7 of DE 28 25 341 shows that the catalyst after the reaction in the presence of the solvent and dibenzylbenzene moderator, which accumulates in the residue after distillation at 80° C. and 0.5 torr and this residue, is reused in two further batch reactions. However, the catalyst displayed a significant loss in activity after use again in a third batch. A need, therefore, continues to exist for a process which enables the recycling of catalyst for effective reuse more than just a few times.

SUMMARY OF THE INVENTION

Accordingly, one object of the present invention is to provide a process for the synthesis of CDT in which the catalyst can be separated and recycled for use in the synthesis of CDT a plurality of times.

Briefly, this object and other objects of the present invention as hereinafter will become more readily apparent can be attained by a process for preparing cyclododecatrienes from 1,3-butadiene in the presence of a catalyst system, which comprises:

reacting 1,3-butadiene in the presence of cyclooctadiene and/or cyclododecatriene in the absence of solvents extraneous to the system in the presence of a catalyst;

separating the crude cyclododecatriene product of the reaction by distillation from the catalyst; and recycling from 50% to 100% of the catalyst system to a reaction medium for cyclododecatriene preparation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
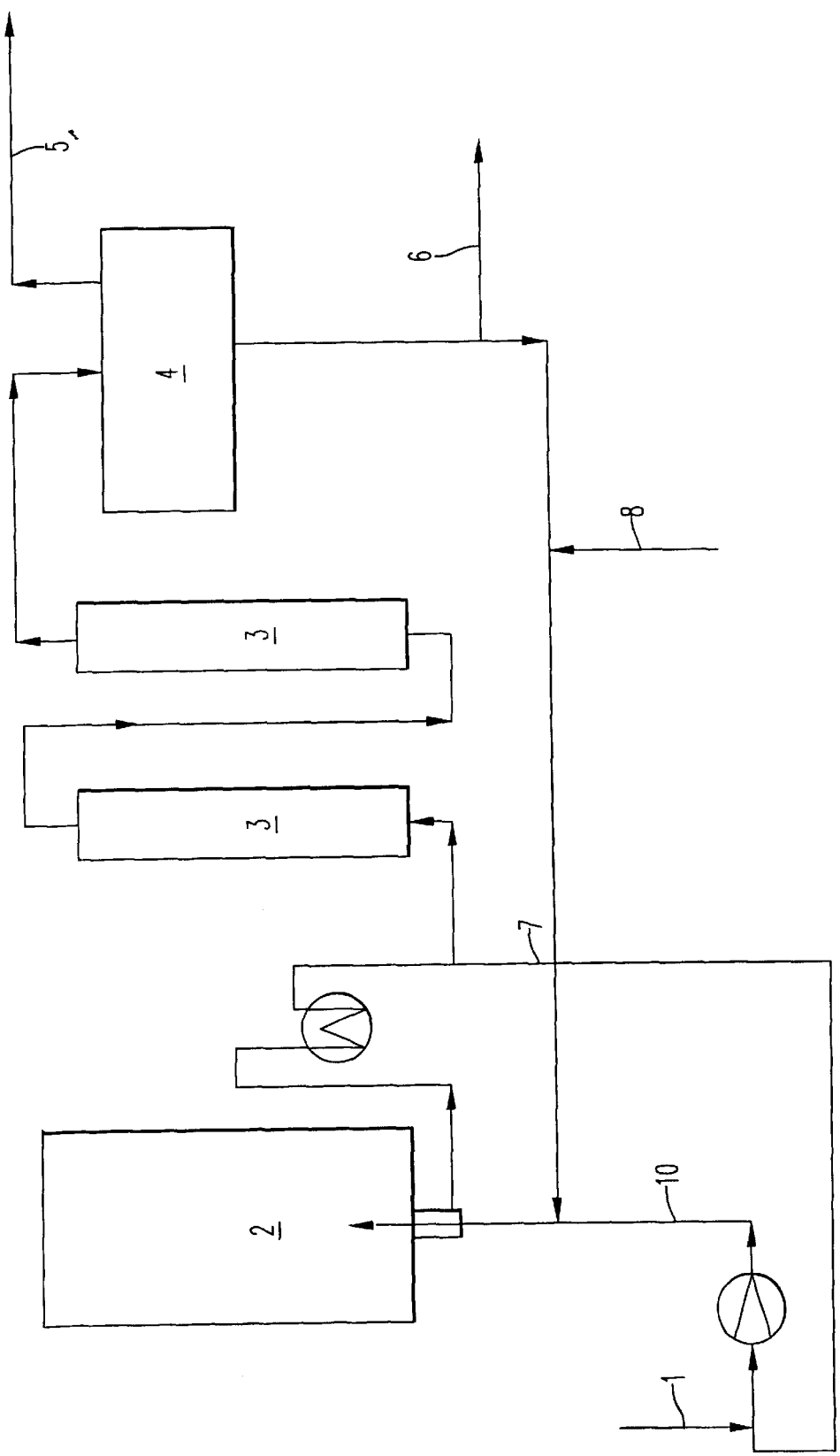
FIG. 1 is a flow diagram of a process system of the invention showing the recycling of catalyst system.

It has now been found that transition metal complexes of CDT and of COD, in particular Ni(0) complexes, are very stable and further, that after separating the crude CDT and the major part of the byproducts (COD, vinylcyclohexene (VCH)) by distillation and partial discharge of the high boilers, can be returned to the process as concentrated catalyst solutions and can be reused.

The invention accordingly provides a process for preparing cyclododecatrienes from 1,3-butadiene in the presence of cyclooctadiene and/or cyclododecatriene using a catalyst comprising, in particular, nickel or titanium, in which process the catalyst system is recycled after removal of the crude cyclododecatrienes by distillation and only the catalyst discharged together with the high boilers is replaced by fresh catalyst.

Catalyst starting materials used are preferably commercial nickel(II)- or titanium(IV)-containing compounds. An example of a starting nickel compound is nickel acetylacetonate and an example of a starting titanium compound is titanium tetrachloride.

The reaction is conducted at catalyst concentrations ranging from 0.01 mmol/l to 40 mmol/l, preferably from 0.05 mmol/l to 10 mmol/l, based on nickel or titanium.

Suitable compounds for activating the catalyst include organometallic compounds of the first-third groups of the Periodic table, preferably compounds of aluminium. Preferred compounds include ethoxydiethylaluminium and ethylaluminium sesquichloride.

The ratio of organometallic compound to the nickel compound is selected so that the molar ratio of nickel to organometallic compound ranges from 1:3 to 1:6.

In the case of titanium, the molar ratio of titanium to oranometallic compound ranges from 1:10 to 1:40. The reaction temperature ranges from 60° C. to 120° C., preferably from 70° C. to 115° C. A temperature higher than 120° C. is to be avoided because a higher proportion of by-products is formed and the catalyst system can be irreversibly damaged at temperatures >120° C.

The recycling of the catalyst (circulation procedure) is shown schematically in FIG. 1 Reaction product discharged from main reactor 2 flows to after-reactors 3. The product material discharged from the after-reactors 3 is depressurized in the vacuum vessel (crude CDT vaporization) 4 at a temperature ranging from 90° C. to 120° C. and a pressure ranging from 2 mbar to 40 mbar where it is fractionated by distillation into residual unreacted butadiene, crude cyclododecatrienes (together with COD and VCH) and high boilers. The distillate from the crude CDT vaporization is passed to final distillation via line 5. After possible discharge of a small part of the catalyst remaining residue (catalyst discharge) from vacuum vessel 4 via line 6, the main part of the catalyst is recirculated via line 7 to a point upstream of the main reactor possibly added by a small amount of fresh catalyst (fresh catalyst addition) via line 8 to replace the catalyst discharged via line 6.

Butadiene feed 1 is pumped through line 10 where it is combined with the catalyst entering main reactor 2.

From 50% to 100%, preferably from 80% to 98%, particularly preferably from 90% to 95%, of the catalyst is recycled.

The reactor system can be charged for the first time, for example, via the butadiene feed line.

The reaction can be conducted batchwise or preferably continuously.

The function of solvent for the catalyst system is performed by materials which are in any case present in the system, i.e. predominantly cyclooctadiene and/or cyclododecatriene. The reaction is thus carried out in the absence of solvents extraneous to the system.

Having now generally described this invention, a further understanding can be obtained by reference to certain specific Examples which are provided herein for purposes of illustration only and are not intended to be limiting unless otherwise specified.

EXAMPLES

The experiments described below were conducted continuously in a plant having a main reactor of 20 m³ capacity and two after-reactors of 1.5 m³ capacity each connected in series.

The amount of catalyst recycled was about 95%.

Gas-chromatographic analyses of the product after pressure release vaporization to final distillation was conducted. A capillary column HP-20M (Carbowax 20M), length: 50 m, diameter: 0.32 mm, film thickness: 30 μm, was used for the separation.

The selectivity to products of the reaction was calculated from the analytical data obtained.

Definition of the Selectivity S using CDT as an Example $$S_{CDT} = \frac{\text{Sum of } CDT \text{ isomers}}{\Sigma COD; VCH; CDT \text{ isomers, high boilers}} \times 100\%$$

The selectivities of the other components are calculated analogously.

Example 1

About 15 m³ of 1,5-cyclooctadiene were placed in the main reactor. Nickel acetylacetonate/ethoxydiethylaluminum was used as the catalyst. After introduction of the calculated amounts of catalyst ($C_{Ni}$=6.7 mmol/l, $C_{Al}$=20 mmol/l), the reactor was heated to 85° C. and 1200 kg/hr of butadiene was fed into the reactor for 3.5 hours to fill the reactor. The feed rate was then reduced to 650 kg of butadiene per hour.

The total conversion of butadiene in the main reactor was about 94%. This level of conversion barely changed in the after-reactors.

The total selectivity for cyclododecatriene was 88.5%.

The selectivities are shown in Table I.

TABLE I

| Selectivities | |
|---|---|
| | % |
| 1,5-Cyclooctadiene | 4.0 |
| Vinylcyclohexene | 4.0 |
| trans-trans-trans-Cyclododecatriene | 69.5 |
| cis-cis-trans-Cyclododecatriene | 11.5 |
| cis-trans-trans-Cyclododecatriene | 7.5 |
| High boilers | 3.5 |

The space-time yield was 5–9 kg of CDT/h·m³.

Example 2

All three reactors were charged with cyclooctadiene and the calculated amount of catalyst ($C_{Ni}$20 mmol/l, $C_{Al}$=60 mmol/l) and heated to 88° C. Butadiene was then fed into the reactors at 1200 kg/h for 30 minutes. The feed rate was then reduced to 500 kg of butadiene per hour.

The conversion of butadiene in the main reactor was 94.3%. In the after-reactors, the total conversion rose to 96.3%.

The total selectivity for cyclododecatriene (trans-trans-trans, cis-cis-trans and cis-trans-trans) was 84%. The selectivities are shown in Table II.

TABLE II

| Selectivities | |
|---|---|
| | % |
| 1,5-Cyclooctadiene | 4.0 |
| Vinylcyclohexene | 4.0 |
| trans-trans-trans-Cyclododecatriene | 64.5 |
| cis-cis-trans-Cyclododecatriene | 11.5 |
| cis-trans-trans-Cyclododecatriene | 8.0 |
| High boilers | 8.0 |

The space-time yield was 14–18 kg of CDT/h·m³.

Example 3

The procedure of Example 2 was repeated, but the temperature employed was 93° C. The total conversion of butadiene in the main reactor was 96.2%. In the after-reactors, the conversion rose to 98%.

The total selectivity for cyclododecatriene (trans-trans-trans, cis-cis-trans and cis-trans-trans) was 90%.

The selectivities are shown in Table III.

TABLE III

| Selectivities | |
|---|---|
| | % |
| 1,5-Cyclooctadiene | 4.5 |
| Vinylcyclohexene | 1.5 |
| trans-trans-trans-Cyclododecatriene | 59.5 |
| cis-cis-trans-Cyclododecatriene | 16.5 |
| cis-trans-trans-Cyclododecatriene | 14.0 |
| High boilers | 4.0 |

The space-time yield was 14–18 kg of CDT/h·m³.

Example 4

The procedure of Example 2 was repeated, but the temperature was 98° C. The total conversion of butadiene in the main reactor was 98.3%. In the after-reactors, the conversion rose to 99.1%.

The total selectivity for cyclododecatriene (trans-trans-trans, cis-cis-trans and cis-trans-trans) was 90.5%.

The selectivities are shown in Table IV.

TABLE IV

| Selectivities | |
|---|---|
| | % |
| 1,5-Cyclooctadiene | 4.0 |
| Vinylcyclohexene | 1.5 |
| trans-trans-trans-Cyclododecatriene | 60.0 |
| cis-cis-trans-Cyclododecatriene | 16.5 |
| cis-trans-trans-Cyclododecatriene | 14.0 |
| High boilers | 4.0 |

The space-time yield was 14–18 kg of CDT/h·m³.

Example 5

A 15 m³ amount of 99.8% pure cyclododecatriene were placed in the main reactor. Titanium tetrachloride and ethylaluminum sesquichloride were used as catalyst system. After introducing the appropriate amount of catalyst ($C_{Ti}$=0.05 mmol/l, $C_{AL}$=2.0 mmol/l ), the reactor was heated to 70° C. and 1200 kg/h of butadiene were fed into the reactor. The total conversion of butadiene was 99%.

The selectivities are shown in Table V.

TABLE V

| Selectivities | |
|---|---|
| | % |
| 1,5-Cyclooctadiene | 1.6 |
| Vinylcyclohexene | 1.2 |
| trans-trans-trans-Cyclododecatriene | 0.7 |
| cis-cis-trans-Cyclododecatriene | 0.1 |
| cis-trans-trans-Cyclododecatriene | 93.4 |
| High boilers | 3.0 |

The disclosure of German priority Application Number 19932577.4 filed Jul. 13, 1999 and 10002460.2 filed Jan. 21, 2000, are hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent:

1. A continuous process for preparing cyclododecatrienes from 1,3-butadiene comprising:

reacting 1,3-butadiene in the presence of a mixture consisting essentially of cyclooctadiene and/or cyclododecatriene and a catalyst system to form a crude cyclododecatriene product comprising cyclododecatrienes;

separating the crude cyclododecatriene product by distillation from the catalyst system; then recycling from 50% to 100% of the catalyst system back into the mixture.

2. The process as claimed in claim 1, wherein from 80% to 98% of the catalyst system is recycled.

3. The process as claimed in claim 2, wherein from 90% to 95% of the catalyst system is recycled.

4. The process as claimed in claim 1, wherein the catalyst system comprises nickel compounds.

5. The process as claimed in claim 4, wherein the catalyst system is prepared from nickel acetylacetonate.

6. The process as claimed in claim 1, wherein the catalyst system comprises titanium compounds.

7. The process as claimed in claim 6, wherein the catalyst system is prepared from titanium tetrachloride.

8. The process as claimed in claim 1, wherein the reaction is carried out at a temperature ranging from 60° C. to 120° C.

9. The process as claimed in claim 8, wherein the reaction is carried out at a temperature ranging from 70° C. to 115° C.

10. The process as claimed in claim 1, wherein a mixture of crude cyclododecatriene, catalyst system, and by-products is depressurized in a vacuum vessel and is fractionated by distillation at a temperature ranging from 90° C. to 120° C. and a pressure ranging from 2 to 40 mbar.

11. The process as claimed in claim 1, wherein high boilers having a boiling point higher than that of 1,3-butadiene, COD, VCH, or CDT formed in the process are discharged from the process during operation and the catalyst discharged together with the high boilers is replaced by the corresponding amount of fresh catalyst system.

12. The process as claimed in claim 1, wherein the catalyst system has a concentration in the mixture of from 0.01 mmol/l to 40 mmol/l of nickel or titanium.

13. The process as claimed in claim 12, wherein the catalyst system has a concentration in the mixture of from 0.05 mmol/l to 10 mmol/l of nickel or titanium.

14. The process as claimed in claim 1, wherein the catalyst system comprises a nickel or titanium compound reacted with an organometallic compound.

15. The process as claimed in claim 14, wherein the organometallic compound is an organoaluminum compound.

16. The process as claimed in claim 15, wherein the organoaluminum compound is ethoxydiethylaluminum or ethylaluminum sesquichloride.

17. The process as claimed in claim 14, wherein the catalyst system comprises a nickel compound reacted with an organoaluminum compound, and the amount of organoaluminum compound provides a molar ratio of nickel to aluminum ranging from 1:3 to 1:6.

18. The process as claimed in claim 14, wherein the catalyst system comprises a titanium compound reacted with an organoaluminum compound, and the amount of organoaluminum compound a molar ratio of titanium to aluminum ranging from 1:10 to 1:40.

19. The process as claimed in claim 1, wherein the organometallic compound comprises a compound having an element of the first through third group of the periodic table.

* * * * *